(12) United States Patent
Acher et al.

(10) Patent No.: US 6,433,014 B1
(45) Date of Patent: Aug. 13, 2002

(54) COMPOUNDS CONSISTING IN PARTICULAR OF EFFECTORS OF THE CENTRAL NERVOUS SYSTEM RECEPTORS SENSITIVE EXCITATORY AMINO ACIDS, PREPARATION AND BIOLOGICAL APPLICATIONS

(75) Inventors: Francine Acher, Vaucresson; Robert Azerad, Ris Orangis; Jean Philippe Pin, Montpellier, all of (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 09/367,311

(22) PCT Filed: Feb. 10, 1998

(86) PCT No.: PCT/FR98/00256

§ 371 (c)(1),
(2), (4) Date: Nov. 29, 1999

(87) PCT Pub. No.: WO98/34907

PCT Pub. Date: Aug. 13, 1998

(30) Foreign Application Priority Data

Feb. 11, 1997 (FR) .............................................. 97 01573

(51) Int. Cl.[7] ........................ A61K 31/195; C07C 61/06
(52) U.S. Cl. ...................................... 514/561; 562/503
(58) Field of Search .......................... 514/561; 562/503

(56) References Cited

U.S. PATENT DOCUMENTS 5,500,420 A 3/1996 Maiese

FOREIGN PATENT DOCUMENTS

WO    WO94/27602    12/1994

OTHER PUBLICATIONS

Database CAPLUS on STN, Acc. No. 1976:477972, Madakyan et al., 'Synthesis of stereoisomeric 2,5–dimethyl–4–aminotetrahydrothiopyran–4–carboxylic acids.' Arm. Khim. Zh. (1976), 29(1), pp. 66–70 (abstract), 1976.*

"Characterization of retinal and hippocampal L–AP4 receptors using conformationally constrained AP4 analogues", Peterson et al., Brain Research 568 (1991) 15–23.

* cited by examiner

Primary Examiner—Brian J. Davis
(74) Attorney, Agent, or Firm—Burns, Doane, Swecker & Mathis, LLP.

(57) ABSTRACT

The invention concerns compounds of formula (I):

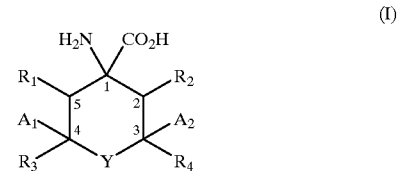

in which: $R_1$ to $R_4$, identical or different, represent hydrogen, alkyl or aryl, themselves substituted if required, $R_1$ and $R_2$ together further capable of representing a bridge —$(CH_2)_m$ in which m is a whole number from 1 to 5, or a bridge X representing a linear combination of m hydrocarbon groups, m being as defined above and comprising, if required, at least a heteroatom such as O, N or S, or a bridge X representing a linear combination of p heteroatoms O, N and/or S, in which p is a whole number from 1 to 3; $A_1$ and $A_2$ represent —COOH, —$SO_3H$ or —$PO_3H_2$ radicals, or their derivatives such as esters or amides, or only one of $A_1$ or $A_2$ has these meanings, when $R_1$ and $R_2$ represent a single bond between the carbons in positions 3 and 4, the other of these groups being a hydrogen atom; Y represents a chain —$(CH_2)_n$—, n being zero or a whole number from 1 to 5, or represents a linear combination of n hydrocarbon groups and at least a heteroatom O, N or S, or a linear combination of q heteroatoms O, N and/or S, in which q is a whole number from 1 to 3. The invention is applicable as medicines.

28 Claims, 6 Drawing Sheets

COMPOUNDS CONSISTING IN PARTICULAR OF EFFECTORS OF THE CENTRAL NERVOUS SYSTEM RECEPTORS SENSITIVE EXCITATORY AMINO ACIDS, PREPARATION AND BIOLOGICAL APPLICATIONS

This application is a 371 of PCT/FR98/00256 filed Feb. 10, 1998/

BACKGROUND OF THE INVENTION

A subjet of the invention is compounds in particular constituting effectors of central nervous system effectors sensitive to neuroexcitatory amino acids (NEAA's), in particular glutamate (Glu), their preparation and their biological uses.

It relates more particularly to agonist, antagonist or reverse agonist compounds of these receptors.

It is known that glutamate is involved in numerous cerebral functions.

Important roles are therefore attributed to glutamatergic receptors, in particular in the conduction of nerve impulse, synaptic plasticity, the development of the central nervous system, learning and memory.

Glutamate is also the main endogenous neurotoxin, being responsible for the neuronal death observed after ischemia, hypoxia, epileptic fits or traumatisms of the brain. It is not therefore surprising that glutamate receptors are considered to be involved in various disorders of the central nervous system and neurodegenerative diseases.

The usefulness can therefore be measured of having means of modulating the effects of the glutamate in the central nervous system by using glutamatergic receptors as targets.

Two main types of glutamatergic receptors have been characterized: ionotropic receptors and metabotropic receptors. The ionotropic receptors are cationic channels activated by the glutamate and directly responsible for the rapid depolarization of post-synaptic cells. They are compounds of different sub-units and classified into three groups according to their pharmacological and functional properties. A distinction is thus made between the NMDA receptors (N-methyl-D-aspartic acid), AMPA (α-amino-3-hydroxy-5-methyl-isoxazole-4-propionic acid) and kainate. Metabotropic receptors (mGluRs) have been revealed more recently (1985), and have been studied in less depth owing to their lack of specific effectors, until the discovery of 1-amino cyclopentane 1,3 dicarboxylic acid or ACPD. They regulate the activity of the ionic channels or enzymes producing second messengers via G proteins binding the GTP. Although they are generally not directly involved in rapid synaptic transmission, these receptors modulate the efficacy of these synapses by regulating either the ionic post-synaptic channels and their receptors, or the release or recapture of the glutamate. The mGluRs therefore play an important role in particular in the induction of the long-term potentialization (LTP) and the long-term depression (LDP) of synaptic transmission, in the regulation of baroceptive reflexes, spatial learning, motor learning, postural and kinetic integration. They are probably also involved in acute or chronic degenerative diseases such as epilepsy, Alzheimer's disease, Parkinson's disease or Huntington's chorea.

To date, eight mGluRs have been cloned and can be classified into 3 groups according to their sequence homologies, their pharmacological properties and their signal transduction mechanisms.

The metabotropic receptors are very useful as targets for the modulation of the effects of glutamate, but their role in various physiological responses involving glutamate remains poorly characterized to date owing to the absence of totally specific tools. Different ligands, analogues of glutamic acid, have been recently described and are used for the pharmacological and physiological characterization of the metabotropic receptors, but turn out to be insufficiently selective and do not allow a perfect differentiation between groups or, within a group, of the sub-group to which the receptor belongs.

There is a requirement for new molecules allowing the differentiation between the ionotropic and metabotropic receptors. It is also important to have more selective molecules available which, within the metabotropic receptor family, allow these receptors to be sought and studied, the bioactive structures specific to each receptor to be defined and new pharmacologically active molecules to be produced.

In this context, the inventors have studied cyclic analogues of glutamic acid with a restricted conformation and have observed that the presence of certain groups in specified positions, with the resulting stereochemical possibilities, led to compounds endowed with strengthened and/or new activities vis-à-vis the glutamatergic receptors.

BRIEF SUMMARY OF THE INVENTION

A purpose of the invention is therefore to provide new compounds endowed with advantageous effects vis-à-vis the receptors of the central nervous system.

It also aims to provide a process for synthesizing these compounds which is easy to implement and can be exploited on an industrial scale.

It also aims to make use of the properties of these new compounds for producing agonist or antagonist agents of these receptors, which can be used as research and study tools, or as medicaments.

The compounds of the invention are characterized in that they correspond to formula (I)

in which
R$_1$ to R$_4$, identical to or different from each other, represent a hydrogen atom, an alkyl radical or an aryl radical, these radicals themselves being substituted where appropriate, R$_1$ and R$_2$ together being able to further represent a —(CH$_2$)$_m$— bridge, where m is an integer from 1 to 5, or a bridge X representing a linear combination of m hydrocarbon groups, m being as defined above, and where appropriate comprising at least one heteroatom such as O, N or S, or a bridge X representing a linear combination of p heteroatoms O, N and/or S, where p is an integer from 1 to 3, A$_1$ and A$_2$ represent —COOH, —SO$_3$H or —PO$_3$H$_2$ radicals or their derivatives such as esters or amides or, when R$_1$ and R$_2$ represent a single bond between the carbons in positions 3 and 4, A$_1$ or A$_2$ has the above meanings, the other of these groups being a hydrogen atom, Y represents a hydrocarbon chain —$(CH_2)_n$—, n being nil or an integer from 1 to 5, or represents a linear combination of n hydrocarbon groups and at least one heteroatom O, N or S, or a linear combination of q heteroatoms O, N and/or S, where q is an integer from 1 to 3.

A preferred family is formed by monocyclic compounds. These are compounds of formula I in which Y and the carbons carrying $R_1$ and $R_2$ are not linked together in forming one of the aforementioned bridges.

In another family of the invention, the compounds are also monocyclic and correspond to formula I above, in which the carbons carrying $R_1$ and $R_2$ are not linked together in forming one of the aforementioned bridges, and Y represents a group or a combination as defined above.

In yet another family of the invention, the compounds are bicyclic and correspond to formula I above in which X or both X and Y are present and are defined as indicated above.

In a preferred group of compounds of these different families, $A_1$ and $A_2$ are identical. In preferred compounds of this group, $A_1$ and $A_2$ both represent a carboxyl group, or the corresponding esters or amides.

In another group, $A_1$ and $A_2$ are as defined above, but are different from each other.

Advantageous compounds of these families and groups include $R_1$, $R_2$, and/or $R_3$ and $R_4$ substituents representing an alkyl or aryl radical, these radicals being substituted where appropriate.

By "alkyl" radical is understood according to the invention a radical of 1 to 10 carbon atoms, in particular 1 to 5 carbon atoms. By "aryl" radical is understood a mono- or polycyclic aromatic radical. A preferred aryl radical is constituted by the phenyl radical.

The alkyl or aryl radicals can be substituted, for example, by a halogen atom or a hydroxyl group.

In other advantageous compounds, $R_1$ and $R_2$ and/or $R_3$ and $R_4$ represent a hydrogen atom.

The compounds defined above can exist as achiral or chiral molecules, in the form of different diastereoisomers, optionally as racemic, where appropriate in the form of one of the enantiomers.

BRIEF DESCRIPTION OF THE DRAWINGS

FIG. 5 shows the reverse agonist effect of ACPT on mGluR1a.

DETAILED DESCRIPTION OF THE INVENTION

The invention in particular relates to 1-aminocyclopentane -1,3,4 tricarboxylic acids ACPT-I, ACPT-II, ACPT-IIIa and ACPT-IIIb which correspond respectively to the following formulae (II), (III), (IVa) and (IVb):

ACPT I = meso-cis ACPT
= (1S, 3R, 4S)

ACPT II = meso-cis ACPT
= (1R, 3R, 4S)

ACPT IIIa =
(-)-(3R, 4R) trans ACPT

ACPT IIIb =
(+)-(3S, 4S) trans ACPT

The invention also relates to a process for synthesizing the compounds defined above.

This synthesis, advantageously carried out according to Bucherer-Bergs' or Strecker's reaction, is characterized in that it comprises operating according to Bucherer-Bergs' technique, the reaction of a ketone of formula (V)

in which $R_1$ to $R_4$ and n are as defined in formula I and $A_3$ and $A_4$ represent a —$COOR_5$, $PO_3(R_5)_2$ $PO_3HR_5$ or $SO_3R_5$ group, where $R_5$ is a hydrogen atom or an alkyl radical, with a cyanide and a basic ammonium carbonate, or operating according to Strecker's technique, the reaction of the ketone (V) with an ammonium salt and a cyanide, then the addition of ammonium carbonate to the reaction mixture, these reactions being carried out under conditions leading to a hydantoin of formula (VI)

(VI)

followed by hydrolysis of the hydantoin thus obtained, or of a hydantoin derivative in which the —NH groups are blocked by protective groups, this hydrolysis leading to obtaining a mixture containing various diastereoisomers, separation of the different compounds, and resolution of the racemics if desired.

In one embodiment, the ketone (V) is reacted with ammonium carbonate and a cyanide, and after a heating stage, the resulting reaction mixture is acidified.

The ketone is in solution in an organic solvent of alcohol type, in particular in methanol.

Amimonium carbonate is used in an excess of 3 to 10 equivalents with respect to the ketone, preferably approximately 5 equivalents.

As an appropriate cyanide, there can be mentioned the mineral cyanides, such as sodium or potassium cyanide. The cyanide is used at a rate of 1 equivalent or in slight excess with respect to the ketone.

The reaction mixture obtained by adding the above compounds, preferably in the form of an aqueous solution, to the ketone is brought to a temperature greater than 40° C. and lower than approximately 90° C.

Heating the mixture can be carried out within a first temperature range, with a cooler, then carried out at a higher temperature, without a cooler, in order to eliminate the excess ammonium salt.

Satisfactory results were obtained by heating the mixture for approximately 8 to 15 hours at approximately 50 to 70° C., in particular at approximately 55–60° C., with a cooler, then at a temperature of the order of 75 to 90° C., for 0.5 to 3 hours, in particular at approximately 80° C., for 1 hour, without a cooler.

The reaction mixture is then acidified. The mixture is subjected for example to agitation after the acid is added, which leads to choosing a reaction time of the order of 10 to 60 minutes, in particular approximately 15 to 30 minutes. The acid is advantageously added in order to obtain a pH of approximately 3 to 4.

In another embodiment, the hydantoins are obtained by firstly adding an ammonium salt, for example ammonium chloride, and a cyanide to the starting ketone (V) in order to form the corresponding aminonitrile derivative, then by adding ammonium carbonate, followed, after reaction, by the acidification of the mixture.

The ketone is then more particularly used in an aqueous solution. The ammonium salt and the cyanide, also in an aqueous solution, are added to the ketone. By operating at ambient temperature, and under agitation, the reaction allowing the corresponding aminonitriles to be obtained is carried out over approximately 1 to 3 days.

Ammonium carbonate is then added to the reaction mixture then, after agitation for several hours, the solution obtained is acidified to a pH of approximately 3 to 4.

The conversion of the hydantoins to the corresponding amino acids is carried out by hydrolysis.

In a variant, an acid or basic solution is added to the hydantoin previously obtained.

Preferably, the acid solution containing the hydantoin is evaporated to dryness beforehand and the residue subjected to an extraction phase in order to eliminate at least part of the salts.

Extraction is carried out for example using an alcohol such as methanol.

The filtrate recovered is evaporated and dissolved in the acid or basic solution and subjected to a heating stage. 2 to 8 N, preferably 6 N hydrochloric acid or sulphuric acid, or 2 to 8 N, preferably 6N soda or potash or barium hydroxide in a saturated solution is advantageously used.

By operating in a closed vessel at a temperature greater than 50° C., in particular approximately 100 to 130° C., in particular of the order of 110° or 120° C., the treatment is carried out over several days, in particular 2 to 6 days.

In another variant, the —NH groups of the hydantoins are first blocked by protective groups, then the derivative obtained in this way is subjected to a controlled basic hydrolysis stage.

The hydantoin solution obtained at the end of the synthesis stage previously described is evaporated to dryness and the resulting hydantoin is esterified, for example by dry 1N HCl in methanol. After evaporation, the residue is taken up in an organic solvent such as ethyl acetate, and washed with a saturated salt solution. The organic phase contains the hydantoin esters.

The esterified hydantoin is subjected to an evaporation stage then a drying stage, and dissolved in an organic solvent such as $CH_3CN$.

In order to block the —NH groups, an alkyl-carbamate is formed in the presence of dimethyl-aminopyridine (DMAP).

This protection is carried out particularly advantageously in the form of butyloxycarbonyl derivatives using di-t-butyldicarbonate (Boc).

After approximately 1 to 2 hours of reaction, the blocked compound is recovered, for example after passage through a chromatography column.

The hydantoin protected in this way is dissolved in acetonitrile, and it is hydrolyzed by adding a base such as lithium hydroxide, preferably in the form of a solution of 1N concentration, followed by neutralization with an acid such as 1N HCl, evaporation to dryness and the residue is treated with an acid solution constituted for example by HCl/$CH_3COOH$.

Separation of the diastereoisomers of the mixture of amino acids is advantageously carried out by chromatography on an anion exchange column.

Advantageously, this stage is preceded by purification carried out by cation exchange chromatography.

Different choices will be made for implementing the process of the invention:
  the choice between Bucherer-Bergs' or Strecker's reaction is dictated by the choice of a preferential cis or trans configuration (position of the —COOH group in position 1 with respect to $A_1$ and $A_2$), (this is the case for example for meso amino acids),
  that of the stereochemistry of the starting ketone by the desired final configuration for the compounds to be synthesized (case of the amino acids where $A_1$ and $A_2$ have a trans relative configuration for example).

Study of the biological activities of the compounds of the invention vis-à-vis the receptors of the central nervous system sensitive to glutamate has demonstrated their specificity vis-à-vis the metabotropic receptors.

Tests carried out using these compounds have in fact shown that they do not display any agonist or antagonist activity on ionotropic receptors (tests carried out at 1 mM on granule cells of the cerebellum, normally activated by NMDA or kainate 100 µM).

On the other hand, these compounds display an agonist or antagonist effect vis-à-vis the metabotropic receptors, as demonstrated by the results given in the examples. According to a very useful aspect, this reaction is selective, for a given compound, with respect to a sub-group of receptors.

Thus, ACPT-I is an agonist of mGluR4. ACPT-II is a general antagonist of all the mGluR's tested (mGluR1a, mGluR2 and mGluR4a) and is endowed with reverse agonist properties on mGluR1. ACTP-IIIa is an antagonist of mGluR4, and ACTP-IIIb an agonist of mGluR4, these two ACTP-IIIa and IIIb being antagonists of mGluR1 and mGluR2.

The invention therefore relates to the use of the compounds defined above as specific agonist or antagonist agents of metabotropic glutamatergic receptors.

These agents can more particularly be used as tools for specifically studying each of the groups and sub-groups of metabotropic receptors by differentiating them and thus allowing definition of their respective specific physiological roles.

Applications based on the use of such tools include the putting the compounds defined above in contact with cell cultures expressing said receptors, under conditions allowing the realization of the agonist, antagonist or reverse agonist reaction to be studied.

The advantageous effects of the compounds of the invention are accompanied by substantial harmlessness as demonstrated by the tests carried out on mice.

The invention therefore relates to the exploitation of the properties of these compounds in acid form, or as pro-drugs, their amides or esters, for the production of pharmaceutical compositions.

The pharmaceutical compositions of the invention are characterized in that they contain an effective quantity of at least one compound as defined above, in combination with an inert pharmaceutical vehicle.

Where appropriate, these compositions contain active ingredients of other medicaments.

The compositions of the invention are particularly suitable for modulating the effect of the glutamate, for example in the treatment of memory disorders, senile dementia, epilepsy, Alzheimer's disease, Parkinson's disease, peripheral neuropathies and motor disorders.

Packaging with a view to sale, in particular labelling and instruction leaflets, and advantageously the wrapping are designed according to the intended therapeutic use.

The pharmaceutical compositions of the invention can be administered in different forms, more particularly by oral or injectable, or also nasal route.

For administration by oral route, use is made in particular of tablets, pills, lozenges, gelatin capsules, drops or also liposomes. These compositions advantageously contain from 1 to 100 mg of active ingredient per unit dose, preferably from 2.5 to 50 mg.

Other forms of administration include solutions which can be injected by intravenous, sub-cutaneous or intramuscular route, produced from sterile or sterilizable solutions. They can also be suspensions or emulsions.

These injectable forms contain from 0.5 to 50 mg of active ingredient, preferably from 1 to 30 mg per unit dose.

For information, the dosage which can be used in man corresponds to the following doses: the patient may thus be given for example from 5 to 300 mg/day, in one or more doses.

Other characteristics and advantages of the invention are given in the following examples in which reference is made to FIGS. 1 to 5 which represent respectively FIGS. 1a to 1c: activation of mGluR receptors by ACPT'S, FIG. 2: inhibition by ACPT's of the formation of IP induced by Glu.

Figure 3A:
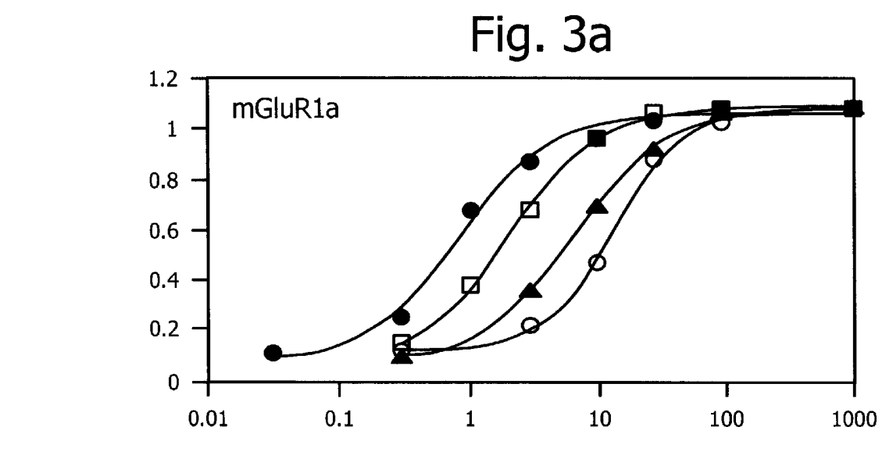
FIGS. 3a to 3c show determination of the antagonist effect and of the ACPT-II inhibition constant, at different concentrations, on the mGluR's, and FIGS. 3d to 3f, the corresponding Shild graphic representations.
Figure 3B:
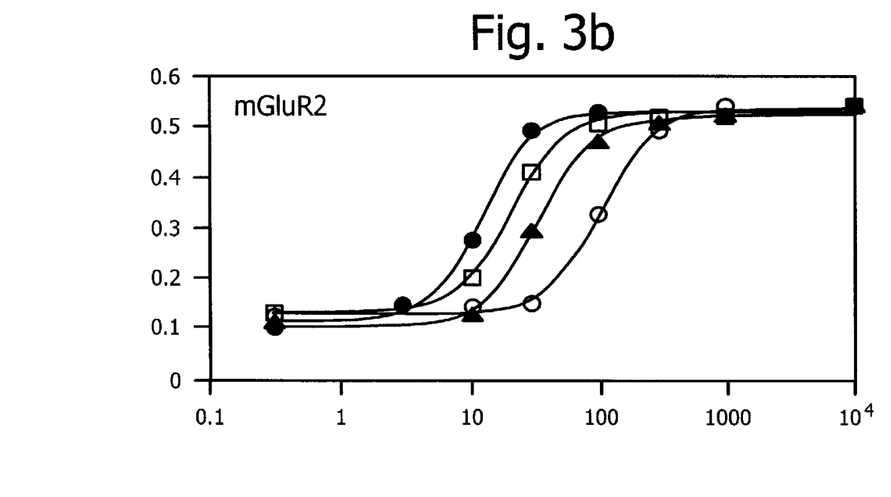
Figure 3C:
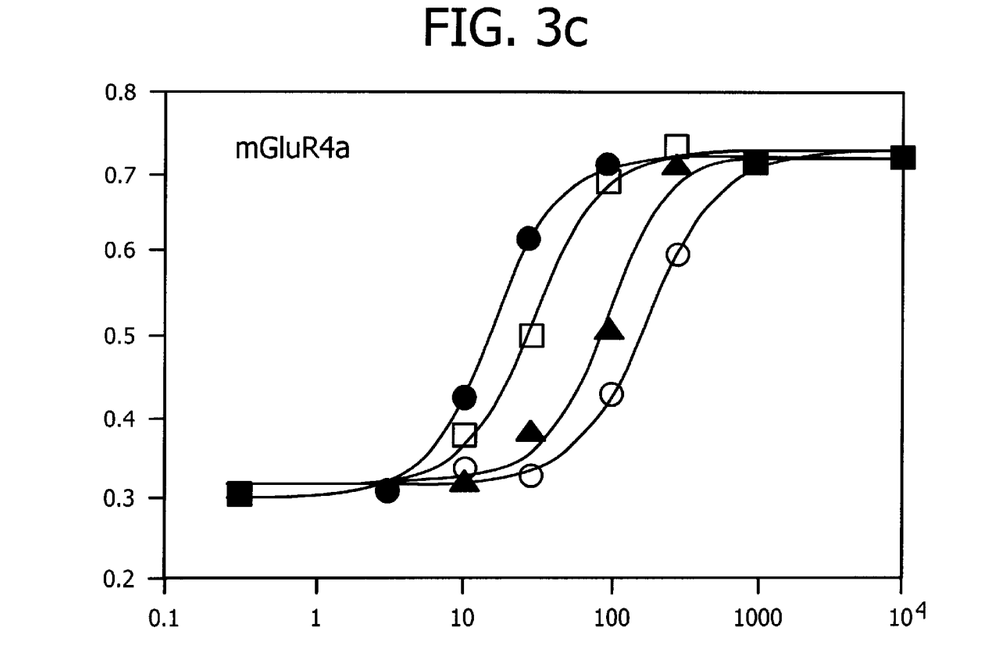
Figure 3D:
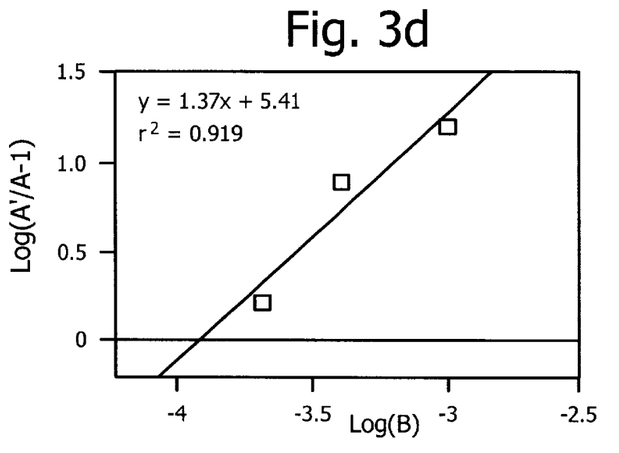
Figure 3E:
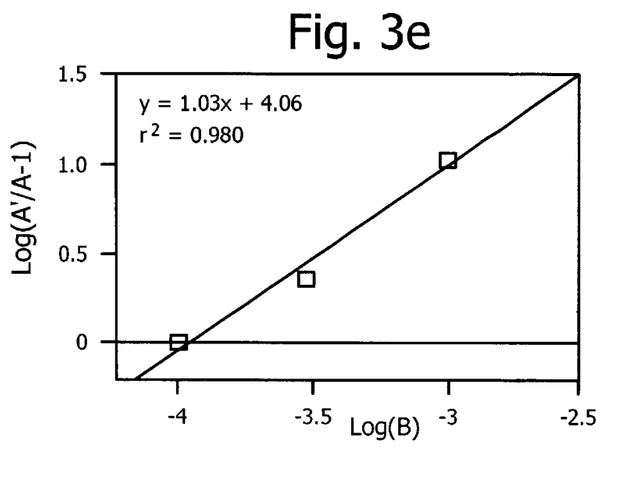
Figure 3F:
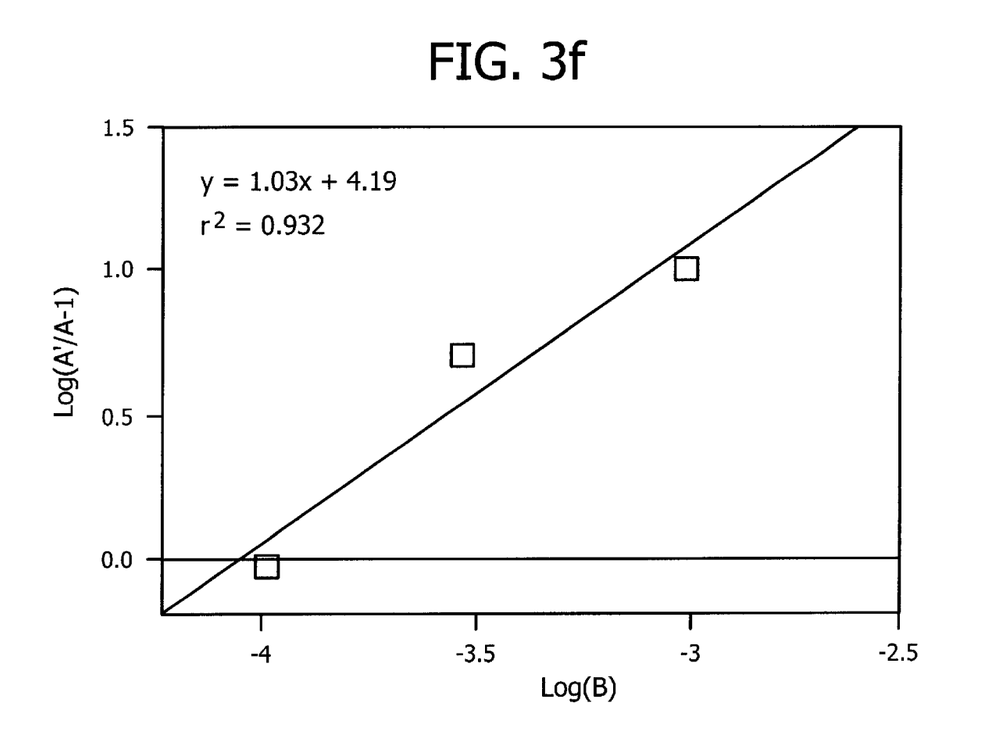
Figure 4A:
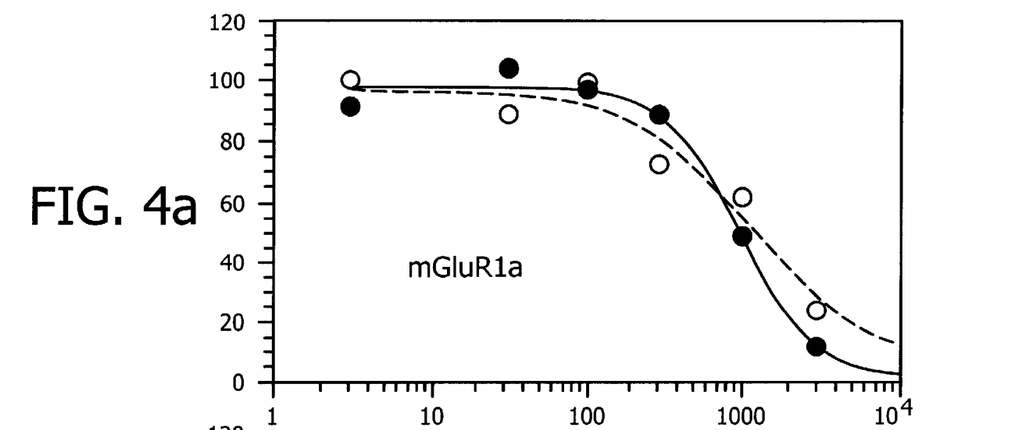
FIGS. 4a to 4c illustrate the antagonist effect of ACPT-III isomers on mGluR's.
Figure 4B:
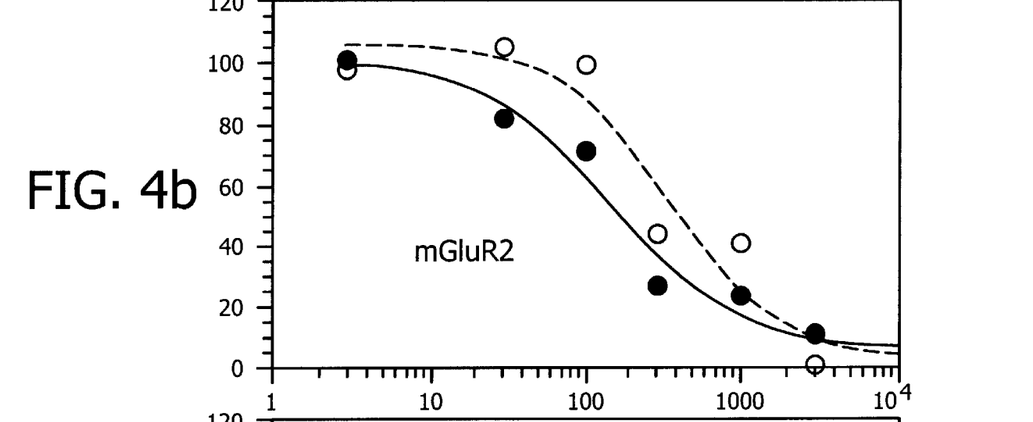
Figure 4C:
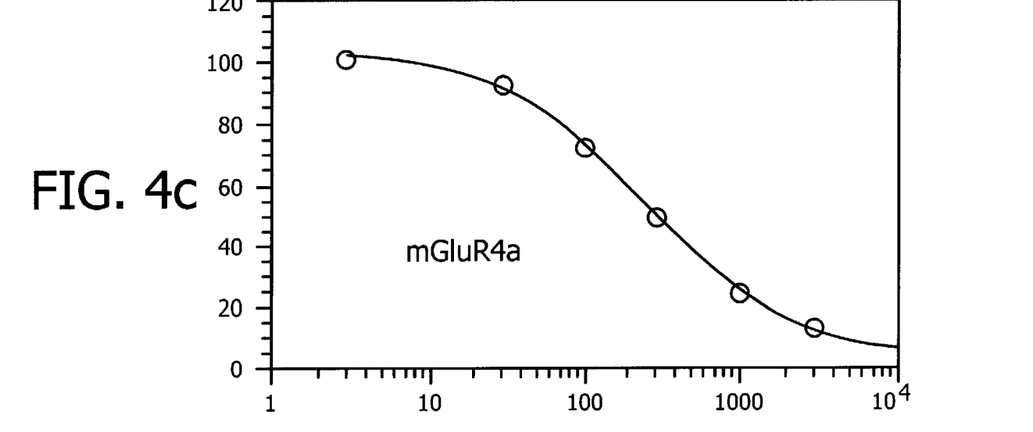

FIGS. 3a to 3c: determination of the antagonist effect and of the ACPT-II inhibition constant, at different concentrations, on the mGluR's, and FIGS. 3d to 3f, the corresponding Shild graphic representations, FIGS. 4a to 4c: the antagonist effect of ACPT-III isomers on mGluR's, and FIG. 5: the reverse agonist effect of ACPT on mGluR1a.

EXAMPLES

These examples relate to ACPT-I (1S, 3R, 4S), ACPT-II (1R, 3R, 4s), (±)-ACPTIII, (3R, 4R)-ACPT-III, and (3S,4S)-ACPT-III. These compounds were synthesized using Bucherer-Bergs' or Strecker's reaction, from 5, (±)-8, (3R, 4R)-8 or (3S,4S)-8 ketoacids (diagrams 1a and 1b, 2 and 3 hereafter), followed by hydrolysis of the hydantoins formed (diagram 4), and separation of the ACPT's by chromatography on an anion exchanger.

Synthesis of the 5 ketodiester

The operation is carried out according to Gais, H. -J.; Bülow, G.; Zatorski, A.; Jentsch, M.; Maidonis, P.; Hemmerle, H. J., *J. Org. Chem.* 1989, 54, 5115–5122; Hemmerle, H., Dissertation, Universität Freiburg im Brisgau, Germany, 1990.

This synthesis is illustrated in the following diagram:

a: $H_2SO_4$/MeOH; b: $KMnO_4$; c:AcONa/$Ac_2O$, 140° C.

Synthesis of the (±)8 ketodiester

The operation is carried out according to Rosenquist, A.; Kvarnström, I.; Svensson, S. C. T.; Classon, B.; Samuelsson, B. *Acta Chem. Scand.* 1992, 46, 1127–1129.

This synthesis is illustrated in the following diagram 1b:

d: sealed tube, 100° C. (Sample, T. E.; Hatch, L. F., *Org. Synth. Coll.* Vol. VI 1988, 454); e: KMnO$_4$; f: AcONa/Ac$_2$O, 140° C.

Synthesis of the (3R,4R)-8 and (3S,4S)-8 ketodiesters.

The operation is carried out according to Suemune, H.; Tanaka, M.; Obaishi, H.; Sakai, K. *Chem. Pharm. Bull.* 1988, 36, 15–21; Rosenquist, A.; Kvarnström, I.; Svensson S. C. T.; Classon, B.; Samuelsson, B. *Acta Chem. Scand.* 1992, 46, 1127–1129.

This synthesis is illustrated in the following diagram 2:

a: pig's liver esterase, pH 7.0; b:CH$_3$N$_2$/CH$_2$Cl$_2$

Synthesis of the hydantoins by Bucherer-Bergs' or Strecker's method, via the corresponding aminonitriles.

Strecker's synthesis, starting from the 5 cis-ketoester, results in the introduction of the aminated group in a slightly more favorable proportion to the product comprising the aminated group in cis position with respect to the carboxylates than Bucherer-Bergs' reaction (ACPT-1, approximately 30% instead of 20%, see Example 4).

This synthesis is illustrated by the following diagram 3:

Conversion of the hydantoins to the corresponding amino acids.

Direct hydrolysis of the hydantoins leads to significant epimerization of one or all of the carboxylic groups in the cis- - - - > trans direction (approximately 25:75 at equilibrium), and can even lead to the racemisation of a trans enantiomer. In order to obtain correct stereochemistry conforming with that of the ketoacid initially used, the method involving the alkaline hydrolysis of the diBoc derivatives of hydantoin (Kubik, S.; Meissner, R. S.; Rebek Jr., J. *Tetrahedron Lett.* 1994, 35, 6635–6638) must be preferred, as it only produces minimum epimerization (or racemisation) (see use in the case of the hydantoin originating from the 5 cis-ketoester, Example 4, or the hydantoins originating from the enantiomerically pure (3R, 4R)-8 or (3S-4S)-8 trans ketoesters, Examples 6 and 7).

This synthesis is illustrated by the following diagram 4:

The detailed syntheses of ACPT's starting from the keto-diesters are reported below.

Example 1

$(NH_4)_2CO_3$ (0.48 g, 5 eq.) and KCN (0.077 g, 1.2 eq.) dissolved in water (1.5 ml) are added to the 5 cis-ketodiester (0.2 g, 1 mmol) dissolved in MeOH 5 (1.5 ml). The mixture is heated overnight at 55–60° C. with a cooler, then for 1 hour at 80° C. without a cooler (in order to eliminate the excess $(NH_4)_2CO_3$) and acidified with a solution of concentrated HCl. The acid solution is agitated for 0.5 hour at ambient temperature. The residue obtained after evaporation to dryness is extracted with MeOH (in order to eliminate part of the salts), the evaporated filtrate (0.23 g) is dissolved in a 6N solution of HCl (20 ml) in a tight screw-topped bottle and heated at 110° C. for 5 days. The solution is evaporated, diluted with 200 ml of water and deposited at an acid pH (approximately pH 2–3) on a Dowex 50×4 cation exchanger column ($H^+$, 20–50 mesh, 2×14 cm). The column is rinsed with water (200 ml) and the mixture of ACPT's eluted with a 0.5 M ammonium hydroxide solution. The fractions which are positive to ninhydrin are evaporated (0.2 g, 0.92 mmol) and the mixture redissolved in boiled water (200 ml) is deposited at a basic pH (approximately pH 9–10) on an AG1×4 anion exchanger column ($AcO^-$, 200–400 mesh, 2×16 cm). After rinsing with boiled water, ACPT-I (10 mg), ACPT-II (30 mg) and (±)-ACPT-III (120 mg) are respectively eluted with a 0.5 M, 0.8 M and 1 M solution of AcOH. Overall yield: 64.1% with respect to the ketodiester.

VPC analysis in the form of N-trifluoroacetyl-O,O'-diisopropyl esters (M. Maurs, C. Ducrocq, A. Righini-Tapie and R. Azerad, *J. Chromatogr.*, 25, 1985, 444–449):

On an OV-1701 capillary column (Flexibond®, Pierce) (15 m×0.2 mm, 0.25 mm film thickness) 190° C.: Rt 13.5 minutes [(±)-ACPT-III], 16.4 minutes (ACPT-II), 19.2 minutes (ACPT-I).

On an Ultra-2® capillary column (Hewlett-Packard) (25 m×0.2 mm; 0.33 mm film thickness, 2 minutes at 140° C., then a gradient from 140 to 300° C. (10° C./min), then 5 minutes at 300° C.: Rt 13.7 minutes ((±)-ACPT-III), 13.9 minutes (ACPT-I), 14.2 minutes (ACPT-II).

On a Chirasil-Val® capillary column (50 m×0.32 mm, 0.2 mm film thickness) 190° C.: Rt 15.0 minutes [(3S,4S)-ACPT-III] and 15.1 minutes [(3R,4R)-ACPT-III], 18.3 minutes [(1S, 3R, 4S)-(ACPT-II)], 22.4 minutes [(1S, 3R, 4S)-(ACPT-I)] 150° C.: Rt 84.7 minutes [(3S,4S)-ACPT-III] and 86.1 minutes [(3R,4R)-ACPT-III].

(1S, 3R, 4S) ACPT-I. GC/MS (EI) m/z (% of basic peak): 352(4), 338(7), 296(30), 268(7), 250(26), 222(100), 204 (16), 177(27).

$^1$H NMR ($D_2O$, $NH_4^+$ salt) : 3.20 (m, 2H, H-3, H-4), 2.63 (m, 2H, H-2, H-5), 2.24 (m, 2H, H-2, H-5).

$^{13}$C NMR: 183.8 and 179.0 (CO), 70.0 (C-1), 50.8 (C-3, C-4), 42.1 (C-2, C-5).

Anal.: calc. for $C_8H_{11}NO_6$, $2H_2O$, %: C, 37.95; H, 5.97; N, 5.53. found, %: C, 38.61; H, 5.46; N, 5.59.

(1R, 3R, 4S) ACPT-II. GC/MS (EI) m/z (% of basic peak): 380(1), 352(12), 338(10), 310(3), 296(21), 268(5), 250(30), 222(100), 204(14), 177(22).

$^1$H NMR ($D_2O$, $NH_4^+$ salt) : 3.33 (m, 2H, H-3, H-4), 2.52 (m, 2H, H-2, H-5), 2.32 (m, 2H, H-2, H-5)

$^{13}$C NMR: 183.6 and 180.4 (CO), 69.2 (C-1), 53.7 (C-3, C-4), 42.3 (C-2, C-5)

Anal: calc. for $C_8H_{11}NO_6$, $2H_2O$, %: C, 37.95; H, 5.97; N, 5.53. found, %: C, 38.53; H, 5.39; N, 5.57.

(±)-ACPT-III. GC/MS (EI) m/z (% of basic peak): 440 (0.01), 380(2), 352(15), 338(8), 310(14), 296(12), 268(65), 250(20), 222(100), 204(18), 177(28).

$^1$H NMR ($D_2O$, $^{30}$ $NH_4$ salt): 3.19 (m, 2H, H-3, H-4), 2.59, 2.42 and 2.10 (3m, 4H, H-2, H-5).

$^{13}$C NMR: 185.9, 183.9 and 179.2 (CO), 69.9 (C-1), 53.2 (C-3, C-4), 43.3 and 42.8 (C-2, C-5).

Anal: calc. for $C_8H_{11}NO_6$, $2H_2O$, %: C, 37.95; H, 5.97; N, 5.53. found, %: C, 38.47; H, 5.31; N, 5.54.

Example 2 cis-ketodiester 5 (0.4 g, 2 mmol) dissolved in MeOH (4 ml) is treated with $(NH_4)_2CO_3$ (0.96 g, 5 eq.) and KCN (0.154 g, 1.2 eq.) as described in Example 1. The residue obtained after evaporation to dryness is dissolved in a suspension of barium hydroxide (3.0 g in 40 ml of water) in a screw-top bottle and heated at 120° C. for 2 days. The solution is cooled down, acidified with a dilute solution of $H_2SO_4$, filtered through celite, diluted with 200 ml of water and deposited on a Dowex 50×4 cation exchanger column (H+, 20–50 mesh, 3×17 cm). The column is rinsed with water (300 ml) and a mixture of ACPT eluted with a 0.5 M ammonium hydroxide solution. The fractions which are positive to ninhydrin are evaporated (0.480 g) and the mixture redissolved in boiled water (250 ml) is deposited at a basic pH on an AG1×4 anion exchanger column ($AcO^-$, 200–400 mesh, 3×19 cm). After rinsing with boiled water, ACPT-I (17.2 mg), ACPT-II (32 mg) and (±)-ACPT-III (324 mg) are eluted with acetic acid solutions as described in Example 1. Overall yield: 75.1%.

Example 3

(NH$_4$)$_2$CO$_3$ (0.96 g, 5 eq.) and KCN (0.154 g, 1.2 eq.) dissolved in water (3 ml) are added to cis-ketodiester 5 (0.40 g, 2 mmol) dissolved in MeOH (4 ml). The mixture is heated at 55–60° C. with a cooler for 2.5 hours then acidified to pH 3≧4 with a solution of dilute HCl. After approximately 15 minutes of agitation at ambient temperature, the solution is concentrated, diluted with an aqueous solution of NaCl (20 ml) and extracted with AcOEt (50 ml×2). The organic phase is dried over Na$_2$SO$_4$, evaporated and dried under vacuum (0.407.g, 1.5 mmol, gross yield 75.4%). Di-t-butyldicarbonate (1.15 ml, 3 eq.) and DMAP (15 mg, 0.08 eq.) [Kubik, S.; Meissner, R. S.; Rebek Jr., J. *Tetrahedron Lett.* 1994, 35, 6635–6638] are added to the mixture of hydantoins dissolved in CH$_3$CN (20 ml). After 1.5 hours, the solvent is evaporated off, the residue taken up in CH$_2$Cl$_2$, rapidly filtered through a small silica column (2×13 cm) and eluted with CH$_2$Cl$_2$ (60 ml), then CH$_2$Cl$_2$/AcOEt (4:1) (150 ml). The diBoc-ester detected on a thin layer using TDM (VonArx, E.; Feyel, M.; Brugger, M. J., *J. Chromatogr.* 1976, 120, 224–228) is evaporated (0.533 g, 1.13 mmol) then dissolved in CH$_3$CN (3 ml) and 1N LiOH (12 ml). The cloudy solution is agitated for 5 hours at ambient temperature, cooled down to 0° C., neutralized with 1N HCl (12 ml) and evaporated to dryness. The residue is treated with a solution of gaseous HCl (~1N) in acetic acid (0.5 hour) then evaporated to dryness. The mixture of ACPT-I, II and III is dissolved in water (1 l) adjusted to pH 4 using NaHCO$_3$ if necessary, purified on a Dowex 50×4 column (H$^+$, 20–50 mesh, 3×17 cm) (0.177 g) then separated on an AG1×4 (AcO$^-$, 200–400 mesh) as described previously, in order to produce ACPT-I (0.035 g), ACPT-II (0.116 g) and (±)-ACPT-III (0.029 g). Overall yield: 36.1 %.

Example 4

NH$_4$Cl (1.08 g, 10 eq.) and KCN (0.13 g, 1 eq.) are added to cis-ketodiester 5 (0.4 g, 2 mmol) dissolved in water (5 ml). After 3 days of agitation at ambient temperature, (NH$_4$)$_2$CO$_3$ is added (0.211 g, 2.2 mmol, 1.1 eq.) and agitation is maintained for 30 hours. The solution is then acidified to pH 4 with 1N HCl and evaporated to dryness. The residue is transferred into a screw-top bottle, suspended in an HCl/MeOH solution (8 ml) and heated for 1.5 hours at 60° C. The insoluble salts are filtered, rinsed with MeOH and the filtrate evaporated and dried under vacuum over KOH (0.742 g). The crude mixture of hydantoin esters is dissolved in AcOEt (20 ml), washed with a saturated solution of NaCl to which NaHCO$_3$ is added in order to maintain a neutral pH. The aqueous washing phase is re-extracted using AcOEt (10 ml). The combined organic phases are dried over Na$_2$SO$_4$ and evaporated. Di-t-butyldicarbonate (1.5 ml, 3 eq.) and DMAP (21 mg, 0.08 eq.) are added to the mixture of methyl esters of hydantoin dissolved in CH$_3$CN (25 ml). The solution is agitated overnight and rapidly purified by flash chromatography (SiO$_2$, 230–400 mesh, 2×10 cm, eluant CH$_2$Cl$_2$, then CH$_2$Cl$_2$/AcOEt, 4:1), leading to a total yield of 53.5% (0.503 g, 1.07 mmol). The mixture of totally protected hydantoins is treated with LIOH, HCl/AcOH, purified and separated as described previously: ACPT-I (0.062 g), ACPT-II (0.096 g), (±)-ACPT-III (0.035 g). Overall yield: 38.8% with respect to the ketodiester.

Example 5

The trans-ketodiester (±)-8 (0.2 g, 1 mmol) is treated as described in Example 1 and leads to ACPT-I (0.015 g), ACPT-II (0.02 g) and (±)-ACPT-III (0.15 g). Overall yield: 74.2% with respect to the ketodiester.

Example 6

The trans-ketodiester-(--)-(3R,4R)-8 (0.134 g, 0.67 mmol, ee>98%) is treated with (NH$_4$)$_2$CO$_3$/KCN, as described in Example 3 for 5 hours, then re-esterified as described in Example 4 in order to produce a colourless oil (0.149 g, 0.552 mmol, yield 82%) which is then treated with Boc$_2$O/DMAP then LiOH and HCl/AcOH and purified as described in Example 3. After the cation exchanger column, a mixture is obtained (0.091 g, 54.1%) essentially containing (−)-(3R,4R)-ACPT-III (97.5%) which is purified by anion exchanger chromatography (0.083 g, 0.333 mmol, ee 99.2%), and small quantities of ACPT-I (0.6%) and ACPT-II (1.9%).

(−−) (3R,4R)-ACPT-III: $[\alpha]_D^{22}$=−32.3 (c 0.73, H$_2$O).

Example 7

The trans-ketodiester-(+)-(3S,4S)-8 (0.172 g, 0.858 mmol, ee>99.8%) is treated as described in Example 6. After the cation exchanger column, a mixture (0.109 g, 50.6%) is obtained essentially containing (+)-(3S,4S)-ACPT-III (98.2%) which is purified by anion exchanger chromatography (0.105 g, 0.451 mmol, ee 98.3%) and small quantities of ACPT-I ((0.4%) and ACPT-II (1.8%).

(+)-(3S,4S)-AcPT-III: $[\alpha]_D^{22}$=+26.4 (c 0.64, H$_2$O)

Example 8
Study of the Biological Activity

The biological activity of ACPT-I, -II and -III was tested on transfected HEK 293 cells expressing mGluR1a, mGluR2 or mGluR4a, chosen as prototypes of the metabotropic receptors of groups I, II or III.

For this purpose, the activation of phospholipase C was measured (accumulation of inositol phosphates).

1) Equipment and methods

Culture and transfection of HEK 293 cells

The HEK 293 cells are cultured in a Dulbecco's modified Eagle medium (DMEM, Gibco BRL) to which 10% of foetal calf serum has been added, and transfected by electroporation as previously described by Gomeza et al., Molecular Pharmacology, 1996, 50:923–930 (1996).

The electroporation is carried out in a total volume of 300 μl with 10 μg of supporting DNA, plasmid DNA containing mGluR1a (0.3 μg), mGluR2 (2 μg) or mGluR4a (5 μg) and 10$^7$ cells.

In order to allow activation of the phospholipase C by mGluR2 and mGluR4a, which effect is easier to measure than the inhibition of the production of cAMP, these receptors are co-expressed with chimeric G, Gqo5 and Gqi9 proteins, as described by Gomeza. The pharmacological profiles of these 2 receptors determined according to this method, have already been described as identical to those characterized by measuring the inhibition of the formation of cAMP.

Determination of the accumulation of inositol phosphates (IP).

The determination of the accumulation of IP in transfected cells is carried out as described by Gomeza after labelling the cells for approximately 14 hours with [$^3$H]-myo-inositol (23.4 Ci/mol, NEN, France).

Stimulation is carried out for 30 minutes in a medium containing 10 mM LiCl in the presence of the drugs tested. The formation of the basic IP is determined after 30 minutes of incubation in the presence of 10 mM LiCl and pyruvate glutamate transaminase (1 U/ml) degrading the glutamate (Glu) and 2 mM of pyruvate in order to avoid the possible effects of Glu released by the cells. The results are expressed in the quantity of IP product with respect to the radioactivity present in the membranes.

Culture and recording of the granule cells of the cerebellum

The granule cells of the cerebellum are cultured from 7 day-old baby mice as described by Van-Vliet, B. J., J. of Neurochemistry, 1989, .52, 1229–1239.

Recording is carried out using the technique known as a "patch clamp" in the full cell configuration and the molecules are applied using a rapid application technique.

2/Results

Initially, tests were carried out in order to check whether the ACPT's were capable of activating or exercising an antagonist effect vis-a-vis the ionotropic receptors. These tests have shown that none of the ACPT enantiomers induces a current when they are placed in contact with the granule cells of the cerebellum at a concentration of 1 mM.

In the same batches, currents are on the contrary seen to be induced by NMDA (100 μM) or kainate (100 μM, which concentration allows activation of both the AMPA and kainate receptors), as envisaged given the activation of the NMDA and non-NMDA receptors. The antagonist effects of ACPT-I, ACPT-II and ACPT-III (1 mM) were also examined in responses induced by NMDA or kainate (100 μM). No significant inhibition was observed with ACPT-II and ACPT-III. On the other hand, a slight inhibition was observed in the presence of ACPT-I (1 mM), of the order of 10%, in the reponses induced by NMDA or kainate.

The effect of the different ACPT's tested was then analyzed on representative mGluRs receptors of groups I, II and III, namely mGluR1a, mGluR2 and mGluR4a.

Figure 1A:
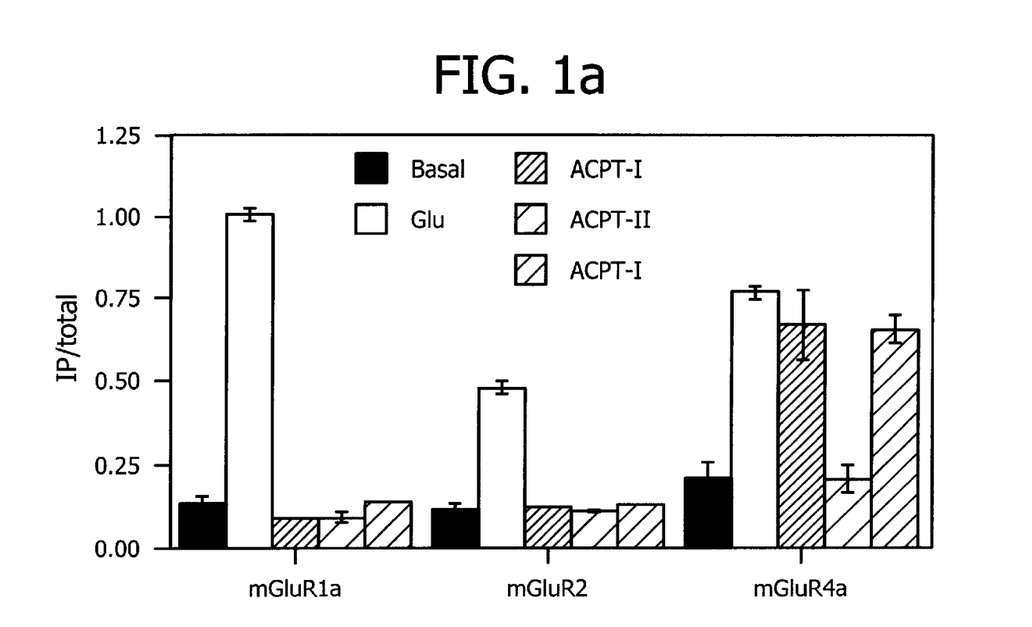
FIGS. 1a to 1c show activation of mGluR receptors by ACPT's.
Figure 1B:
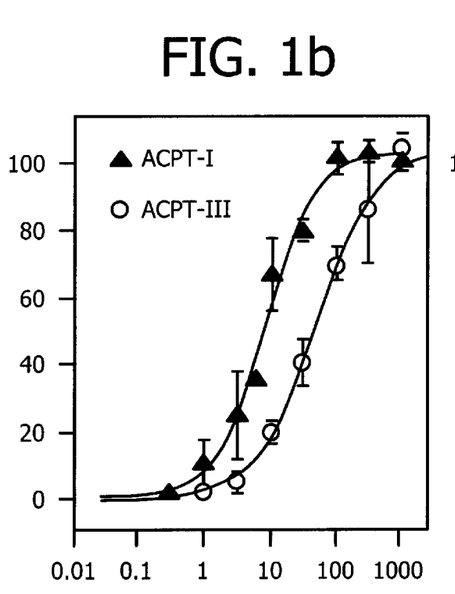
Figure 1C:
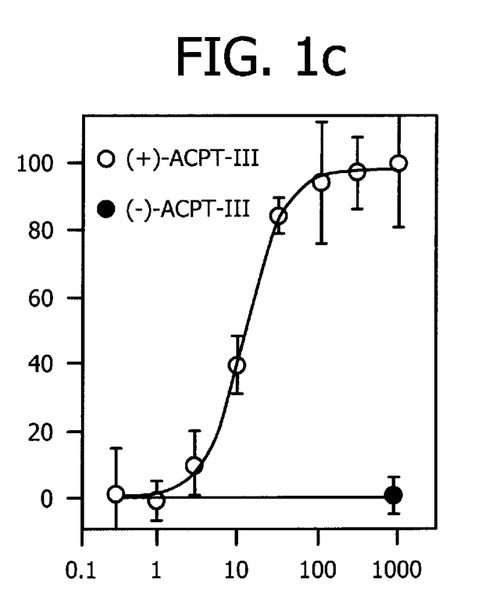

The results obtained are illustrated by FIGS. 1a to 1c and summarized in Table 2.

FIG. 1a indicates the accumulation of inositol phosphates (IP) induced by these molecules (3 mM), compared with that induced with by (Glu) at a concentration of 1 mM. In this figure, ■ represents the basic values (IP), □ represents those measured in the presence of Glu, ▨ in the presence of ACPT-I, ▧ in the presence of ACPT-II and ▨ in the presence of ACPT-III.

FIGS. 1b and 1c give the IP production response, expressed in % of the maximum effect, as a function of the concentration of the medicament used in μM.

FIG. 1b indicates the agonist effect of ACPT-I (▲) and (±)ACPT-III (○), at different concentrations, on mGluR4a and FIG. 1c the agonist effect for enantiomers of ACPT-III (○: (+)ACFT-III; ●: (−)ACPT-III, at different concentrations, on mGluR4a.

As FIG. 1a shows, none of the ACPT molecules activates MGluR1a or mGluR2.

On the other hand, ACPT-I and ACPT-III activate mGluR4a in a dose-dependent manner (FIGS. 1a and 1b) with $EC_{50}$ values (effective concentration producing 50% of the maximum effect), respectively, of 7.2±2.3 and 40±8 μM (n=3).

It can be noted that only (+)ACPT-III has agonist properties vis-à-vis mGluR4a with an $EC_{50}$ value of 8.8±3.2 μM (n=2) (FIG. 1c).

Figure 2:
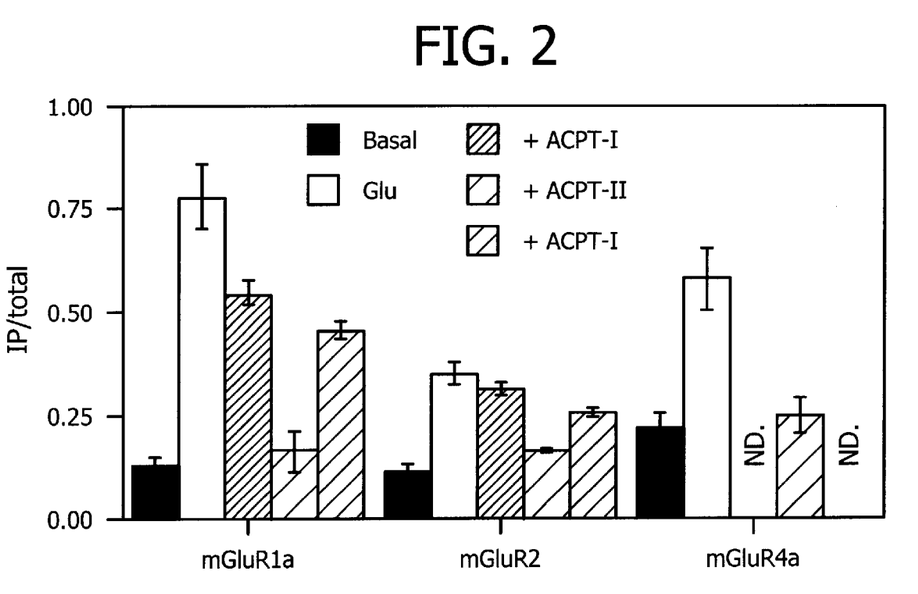
FIG. 2 illustrates inhibition by ACPT's of the formation of IP induced by Glu.

FIG. 2 shows the inhibition of the formation of I? induced by Glu, under the effect of the ACPT's (the symbols are the same as in FIG. 1a).

It can be noted that ACPT-I, -II, and -III inhibit the formation of the IP's induced by the Glu in cells expressing mGluR1a. All these compounds induce a move to the right of the dose-response curve of the Glu as expected for competitive antagonists.

It can be noted that the compounds ACPT-II and -III also inhibit the responses induced by Glu in cells expressing mGluR2. This result is not obtained with ACPT-I. ACPT-II appears to be more active than ACPT-III.

It can also be noted that the ACPT-II compound also exercises an antagonist effect vis-à-vis the effect of Glu on mGluR4a and therefore appears as a general antagonist of the metabotropic glutamatergic receptors.

All the above results are summarized in Table 2 below where the agonist ($EC_{50}$, μM) or antagonist ($K_B$, μM) effect of the ACPT's on the mGluR1a, mGluR2 and mGluR4a receptors is indicated.

| | mGluR1a | | mGluR2 | | mGluR4a | |
|---|---|---|---|---|---|---|
| | $EC_{50}$ | $K_B$ | $EC_{50}$ | $K_B$ | $EC_{50}$ | $K_B$ |
| ACPT-I | — | >1000 | — | — | 7.2 ± 2.3 | — |
| ACPT-II | — | 115 ± 2 | — | 88 ± 21 | — | 77 ± 9 |
| (=)-ACPT-III | — | >300 | — | >300 | 40 ± 8 | — |
| (+)-(3S, 4S)-ACPT-III | — | (1000)[a] | — | (150)[a] | 8.8 ± 3.2 | — |
| (−)-(3R, 4R)-ACPT-III | — | (1000)[a] | — | (300)[a] | — | 220 |

"—"; no activity at the highest concentration tested (3 mM).
[a]$IC_{50}$ values (Glu = 20 μM for mGluR1a and mGluR2, 30 μM for mGluR4a)

FIGS. 3a to 3c and 3d to 3f illustrate tee antagonist effect, and the determination of the inhibition constant of ACPT-II on the mGluR1a receptors (FIGS. 3a and 3d), mGluR2 (FIGS. 3b, and 3e) and mGluR4a (FIGS. 3c and 3f). FIGS. 3a to 3c give the production of IP (with respect to the total radioactivity, in gross values), as a function of the concentration of Glu in μM (logarithmic scale), used alone (control) or in the presence of a fixed concentration of ACPT-II. The symbols have the following meanings: (●), control; (□), +100 μM (200 μM for mGluR1a); (▲), +300 μM (500 μM for mGluR1a); ○, +1000 μM.

The graphs of FIGS. 3d to 3f show Shild's graphic representation obtained from the dose-response curves of FIGS. 3a to 3c and give the values of Log(A'/A−1) as a function of Log (B), where A' is the $EC_{50}$ value of the Glu measured in the presence of concentration B of ACPT-II and A, the $EC_{50}$ value of the Glu measured in the absence of ACPT-IT, i.e. in the absence of an antagonist.

It can be noted that the ACPT-II compound exercises a similar effect on mGluR1a, mGluR2 and mGluR4a. In each case, the slope is close to the unit as envisaged for a competitive antagonist. The respective KB values determined using Shild's representation are 115±2, 88±21, 77±9 μM (n=3) respectively for mGluR1a, mGluR2 and mGluR4a.

The effect of (+) ACPT-III and (−) ACPT-III on these receptors was also studied, taking into account the activity of the ACPT-III, formed by the two enantiomers, on mGluR1a and mGluR2.

The optional antagonist effect of the (−)ACPT-III compound on mGluR4a was also studied, given that only the (+) enantiomer is an agonist of this receptor as indicated above.

The results obtained are reported in FIGS. 3a to 3c. These figures respectively concern the results obtained on mGluR1a, mGluR2 and mGluR4a. The symbols are the following: (●) antagonist effect of the compound (+) ACPT-III and (○) of the compound (−) ACPT-III on mGluRs. The concentrations in ACPT-III are expressed in μM units.

It can be noted that the ACPT-III (+) and (−) inhibit the Glu responses, with a low strength in the cells expressing mGluR1a or mGluR2. On mGluR4a, the (−) ACPT-III compound exercises an antagonist effect vis-à-vis that of Glu (FIG. 4c) and analysis of the Shild curves indicates a competitive inhibition (slope=0.877) with a $K_B$ value of 220 µM.

Figure 5A:
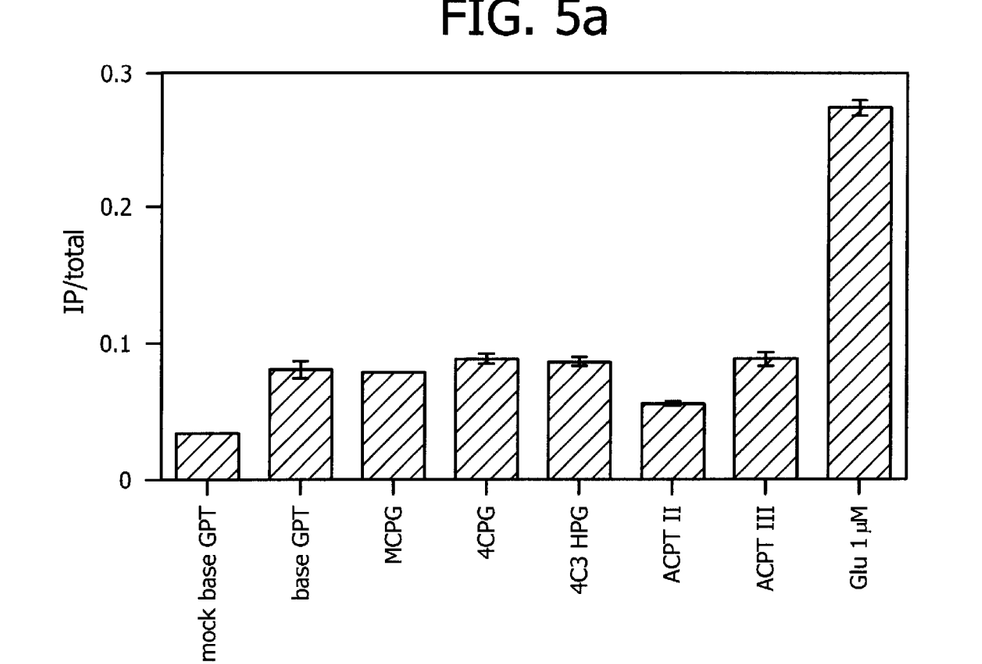
Figure 5B:
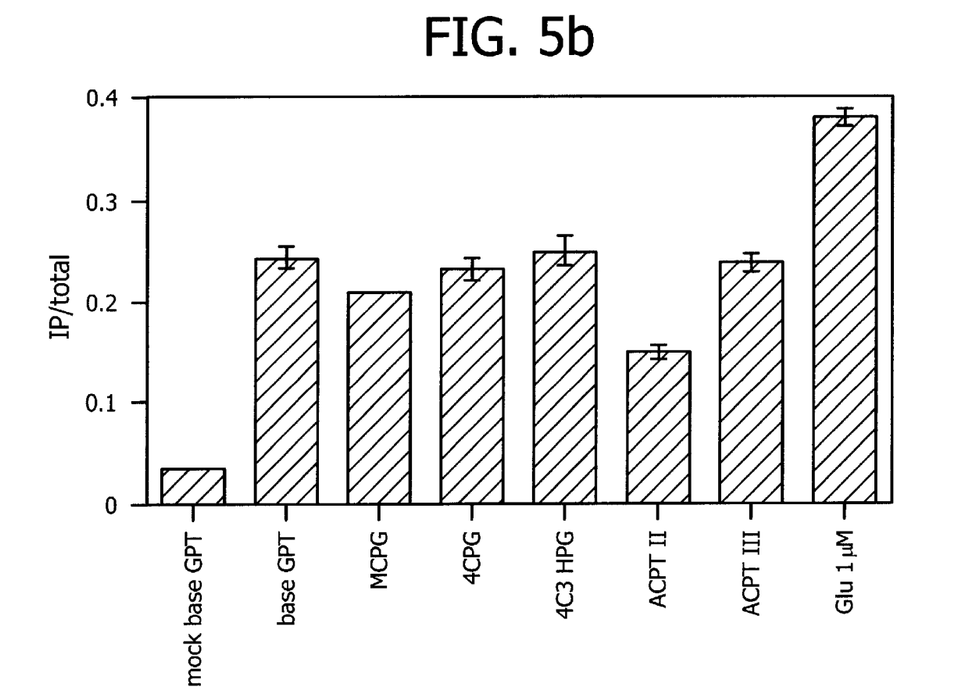

As already described with numerous other receptors coupled to G proteins, it is possible to detect a basic activity of the mGluR1a receptor (Prézeau et al., Molecular Pharmacology, 1996, 49:422–429). In fact, even in the total absence of any agonist, an increased activity of the phospholipase C is detectable in cells expressing mGluR1a. However, unlike what is observed with other receptors coupled to G proteins, none of the known competitive antagonists of mGluR1 is capable of inhibiting the constitutive activity of this receptor. None of these molecules therefore acts as a reverse agonist. On the other hand, the use of ACPT-II (but not of ACPT-I or ACPT-III) at a concentration of 1 mM inhibits the basal activity of mGluR1a measured either under control conditions, or when the receptor is co-expressed with the alpha sub-unit of the Gq protein. These results are reported in FIGS. 5a and 5b. In FIG. 5a, it can be seen that only ACPT-II significantly inhibits the basal activity of the phospholipase C measured on HEK 293 cells expressing the mGluR1a receptor. FIG. 5b shows the results obtained on cells expressing mGluR1a and overexpressing the alpha sub-unit of the Gq protein. These observations show that ACPT-II is the only known antagonist of mGluR1a endowed with a reverse agonist activity on this receptor.

What is claimed is:

1. A compound which is an agonist, antagonist or reverse agonist of glutamatergic receptors, of formula (I)

(I)

in which
R$_1$ to R$_4$, identical to or different from each other, represent a hydrogen atom, an alkyl radical or an aryl radical, said radicals being optionally substituted, R$_1$ and R$_2$ together being able to further represent a —(CH$_2$)$_m$— bridge, where m is an integer from 1 to 5,
A$_1$ and A$_2$ each represent a radical selected from the group consisting of —COOH, —SO$_3$H and —PO$_3$H$_2$ radicals and their amide and ester derivatives,
Y represents a hydrocarbon chain —(CH$_2$)$_n$—, n being 0 or an integer from 1 to 5, said hydrocarbon chain optionally including at least one heteroatom O, N or S.

2. A compound according to claim 1, wherein the carbons carrying R$_1$ and R$_2$ are not linked together to form a bridge and Y is —(CH$_2$)$_n$— where n is 0.

3. A compound according to claim 1, wherein the carbons carrying R$_1$ and R$_2$ are not linked by a bridge and Y represents a —(CH$_2$)$_n$— group where n is an integer from 1 to 5.

4. A compound according to claim 1, wherein A$_1$ and A$_2$ both represent a carboxyl group, or a derivative thereof, wherein said derivative is selected from the group consisting of ester and amide derivatives.

5. A compound according to claim 1, wherein R$_1$ to R$_4$ represent a hydrogen atom.

6. A compound according to claim 1, wherein said compound is an achiral or chiral molecule in the form of a diastereoisomer.

7. A compound according to claim 5, wherein said compound is a 1-amino-cyclopentane 1,3,4 tricarboxylic acid selected from the group consisting of ACPT-I, ACPT-II, ACPT-IIIa and ACPT-IIIb respectively corresponding to the following formulae (II), (III), (IVa) and (IVb):

(II)  (III)
ACPT I = meso-cis ACPT  ACPT IIIb = meso-trans ACPT
= (1S, 3R, 4S)  = (1R, 3R, 4S)

(IVa)  (IVb)
ACPT IIIa =  ACPT IIIB =
(−)-(3r-4r) trans ACPT  (+)-(3S,4s)trans ACPT.

8. Process for synthesizing a compound according to claim 1 comprising:
reacting a ketone of formula (V)

in which R$_1$ to R$_4$ and n are as defined in formula I and A$_3$ and A$_4$ represent a —COOR$_5$, PO$_3$(R$_5$)$_2$, PO$_3$HR$_5$, or SO$_3$R$_5$ group, where R$_5$ is a hydrogen atom or an alkyl radical,
with a cyanide and a basic ammonium carbonate, or
reacting the ketone (V) with an ammonium salt and a cyanide, then adding ammonium carbonate to the reaction mixture, said reaction producing a hydantoin of formula (VI)

followed by hydrolysis of the hydantoin thus obtained, or of a hydantion derivatives in which the —NH groups are blocked by protective groups, said hydrolysis resulting in a mixture containing various diastereoisomers, and
separating the different compounds.

9. A pharmaceutical composition comprising at least one compound according to claim 1, in combination with a pharmaceutically acceptable vehicle.

10. A compound according to claim 1, wherein at least one of R$_1$ to R$_4$ is an alkyl radical or an aryl radical.

11. A compound according to claim 10, wherein said radical is substituted.

12. A compound according to claim 11, wherein said radical is substituted with a halogen atom or a hydroxyl group.

13. A compound according to claim 3, wherein Y is a hydrocarbon chain —$(CH_2)_n$— where n is an integer from 1 to 5, said hydrocarbon chain having at least one heteroatom O, N and/or S between said $(CH_2)_n$ groups when n is an integer from 2 to 5.

14. A compound according to claim 4, wherein said carboxyl group derivative is selected from the group consisting of ester and amide derivatives.

15. A compound according to claim 6, wherein said diastereoisomer is racemic.

16. A compound according to claim 15, wherein said diastereoisomer is in the form of an enantiomer.

17. Process according to claim 8, further comprising resolution of racemic diastereoisomers.

18. A method for producing an agonist, antagonist or reverse agonist effect on a glutamatergic receptor comprising administering a compound according to claim 1 to a glutamatergic receptor.

19. A method according to claim 18, wherein said glutamatergic receptor is a metabotropic glutamatergic receptor.

20. A method for producing an agonist, antagonist or reverse agonist effect on a glutamatergic receptor in a cell culture comprising introducing a compound according to claim 1 to a cell culture expressing said receptors.

21. A method according to claim 20, wherein said glutamatergic receptor is a metabotropic glutamatergic receptor.

22. A pharmaceutical composition according to claim 9, wherein said compound of formula I is in the form of a prodrug.

23. A pharmaceutical composition according to claim 9, wherein said compound of formula I is in the form of an amide or ester.

24. A method for modulating an effect of glutamate in a central nervous system of a patient comprising administering a compound according to claim 1 in an amount effective for modulating the effect of glutamate.

25. A method for treating a condition selected from the group consisting of memory disorders, senile dementia, epilepsy, Alzheimer's disease, Parkinson's disease, peripheral neuropathies and motor disorders in a patient comprising administering to said patient a compound according to claim 1 in an amount effective for treating said condition.

26. A pharmaceutical composition comprising the compound according to claim 1 in an amount effective for producing an agonist, antagonist or reverse agonist effect on a glutamatergic receptor, in combination with a pharmaceutically acceptable vehicle.

27. A pharmaceutical composition comprising the compound according to claim 1 in an amount effective for modulating an agonist, antagonist or reverse agonist effect of glutamate on the glutamatergic receptors of a central nervous system of a patient, in combination with a pharmaceutically acceptable vehicle.

28. A pharmaceutical composition comprising the compound according to claim 1 in an amount effective for treating a condition selected from the group consisting of memory disorders, senile dementia, epilepsy, Alzheimer's disease, Parkinson's disease, peripheral neuropathies and motor disorders in a patient, in combination with a pharmaceutically acceptable vehicle.

* * * * *